US009622794B2

(12) United States Patent
Tuten (10) Patent No.: US 9,622,794 B2
(45) Date of Patent: Apr. 18, 2017

(54) POLYAXIAL PEDICLE SCREW LOCKING AND DEROTATION INSTRUMENT

(71) Applicant: Hans Robert Tuten, Richmond, VA (US)

(72) Inventor: Hans Robert Tuten, Richmond, VA (US)

( * ) Notice: Subject to any disclaimer, the term of this patent is extended or adjusted under 35 U.S.C. 154(b) by 138 days.

(21) Appl. No.: 14/628,612

(22) Filed: Feb. 23, 2015

(65) Prior Publication Data

US 2015/0238235 A1    Aug. 27, 2015

Related U.S. Application Data

(60) Provisional application No. 61/943,554, filed on Feb. 24, 2014.

(51) Int. Cl.
*A61B 17/70*    (2006.01)

(52) U.S. Cl.
CPC ................................ *A61B 17/7077* (2013.01)

(58) Field of Classification Search
CPC ............ A61B 17/7077; A61B 17/7079; A61B 17/708; A61B 17/7082
USPC ................................ 606/86 R, 86 A, 99, 104
See application file for complete search history.

(56) References Cited

U.S. PATENT DOCUMENTS

| 5,707,371 A * | 1/1998 | Metz-Stavenhagen | A61B 17/861 606/104 |
| 6,440,133 B1 * | 8/2002 | Beale | A61B 17/7086 606/104 |
| 2012/0089150 A1 * | 4/2012 | Smith | A61B 17/7076 606/104 |

* cited by examiner

*Primary Examiner* — Ellen C Hammond
*Assistant Examiner* — Christina Negrellirodrigue
(74) *Attorney, Agent, or Firm* — Clements Bernard Walker PLLC; Christopher L. Bernard; Lawrence A. Baratta, Jr.

(57) ABSTRACT

A pedicle screw locking and derotation instrument, comprising: an elongate actuation mechanism, wherein the elongate actuation mechanism comprises a pair of elongate arms that are pivotably hinged to one another and comprise a pair of handle portions; and a pair of clamp members coupled to the elongate actuation mechanism and deployed by actuation of the elongate actuation mechanism; wherein each of the pair of clamp members comprises a retention portion configured to selectively and securely engage a threaded shaft of a pedicle screw and a portion configured to selectively and securely engage a head body of the pedicle screw, thereby holding the threaded shaft and the head body in rigid alignment; wherein each of the pair of clamp members comprises a retention portion that is configured to be selectively disposed beneath the head body of the pedicle screw and about the threaded shaft of the pedicle screw.

19 Claims, 11 Drawing Sheets

POLYAXIAL PEDICLE SCREW LOCKING AND DEROTATION INSTRUMENT

CROSS-REFERENCE TO RELATED APPLICATION

The present patent application/patent claims the benefit of priority of U.S. Provisional Patent Application No. 61/943,554, filed on Feb. 24, 2014, and entitled "POLYAXIAL PEDICLE SCREW LOCKING AND DEROTATION INSTRUMENT," the contents of which are incorporated in full by reference herein.

FIELD OF THE INVENTION

The present invention relates generally to a polyaxial pedicle screw locking and derotation instrument for grasping and derotating the vertebrae of the spine in a surgical scoliosis correction procedure or the like.

BACKGROUND OF THE INVENTION

It is a common procedure to derotate the individual vertebra of the spine during a surgical scoliosis correction procedure or the like. This typically occurs once the spinal rods have been inserted into the pedicle screws that have been implanted. Such a surgical scoliosis correction procedure typically consists of 4 main steps:
1. Decortication of the spinal column. This consists of the removal of bone to loosen up the vertebral bodies so that they can be easily manipulated and straightened.
2. Insertion of the pedicle screws into the vertebra, as is done conventionally.
3. Insertion of the spinal rods and set screws into the pedicle screws to straighten the spine.
4. Rotation of the individual vertebral bodies along the spinal axis using the pedicle screws.

During a typical surgical scoliosis correction procedure it is not uncommon for the individual vertebra to be twisted along the spinal column. Although the spinal rods correct and straighten the spinal column, the individual vertebra can still be rotated along the axial plane. Typically, in conventional procedures, derotation tubes are placed over the heads of the implanted pedicle screws and are used to derotate each individual vertebra, which are then locked into position by tightening the set screw in each head body, locking the spinal rods into place. It should be noted that, as used herein, 'rotation' and 'derotation' are essentially synonymous, with the individual vertebra initially being rotated and subsequently being derotated via rotation of the associated pedicle screws.

This method works well if a surgeon is using monoaxial pedicle screws in the vertebrae. A monoaxial pedicle screw has a head body that is fixed to the threaded shaft with limited degrees of freedom, such that the whole vertebra can be derotated using the pedicle screw as a rigid lever arm. A problem arises, however, when the surgeon has placed a polyaxial pedicle screw with multiple degrees of freedom in the individual vertebra and attempts to derotate the individual vertebra; only the head body rotates as there is designed pivotal movement between the head body and the threaded shaft. There is no rigid lever arm by which to derotate the individual vertebra. Thus, in most cases, it is very difficult to derotate a vertebral body using a polyaxial pedicle screw, as the heads body moves or pivots, but the individual vertebra does not.

Thus, what is still needed in the art is an instrument that addresses this problem with polyaxial pedicle screws in such procedures.

BRIEF SUMMARY OF THE INVENTION

In various exemplary embodiments, the present invention provides a polyaxial pedicle locking and derotation instrument that allows a surgeon to be able to successfully rotate both a monoaxial pedicle screw and a polyaxial pedicle screw, and thereby derotate an individual vertebra using a rigid lever arm. This is achieved as the instrument grabs onto both the smooth portion of the threaded shaft just below the head body of the pedicle screw, and at the same time grabs and secures the head body. This prevents the head body from 'flopping over' as the head body and the pedicle screw now act as a single unit. Rotation of the instrument causes both the head body and the threaded shaft of the pedicle screw to be successfully rotated. Effectively, the instrument causes the polyaxial pedicle screw to become a monoaxial screw by locking the two components together during manipulation.

The instrument generally consists of the following components:
1. A forceps type instrument with two handles and a locking ratchet to lock the instrument in place once the two handles have been squeezed together.
2. A scissor type hinge to allow the two clamps and handles to pivot about.
3. Two lower clamps that wrap around the head body and the top section of the pedicle screw where it enters into the head body.
4. Squeezing of the two handles causes the two lower clamps to rigidly hold the head body and upper smooth portion of the threaded shaft. This action locks the head body and threaded shaft together, preventing independent movement.

In one exemplary embodiment, the present invention provides a pedicle screw locking and derotation instrument, comprising: an elongate actuation mechanism; and a pair of clamp members coupled to the elongate actuation mechanism and deployed by actuation of the elongate actuation mechanism; wherein each of the pair of clamp members comprises a portion configured to selectively and securely engage a threaded shaft of a pedicle screw and a portion configured to selectively and securely engage a head body of the pedicle screw, thereby holding the threaded shaft and the head body in rigid alignment. The elongate actuation mechanism comprises a pair of elongate arms that are pivotably hinged to one another and comprise a pair of handle portions. The instrument also includes ratcheting mechanism coupling the pair of elongate arms. The pair of clamp members are pivotably hinged to the pair of elongate arms. The pair of clamp members are pivotably hinged to one another. Each of the pair of clamp members comprises a retention portion that is configured to be selectively disposed beneath the head body of the pedicle screw and about the threaded shaft of the pedicle screw. The pair of clamp members collectively define a void that is disposed about and substantially conforms to the head body of the pedicle screw. The elongate actuation mechanism is operable for imparting rotational motion to the pedicle screw and an individual vertebra in which the pedicle screw is implanted.

In another exemplary embodiment, the present invention provides a pedicle screw locking and derotation instrument, comprising: an elongate actuation mechanism, wherein the elongate actuation mechanism comprises a pair of elongate arms that are pivotably hinged to one another and comprise a pair of handle portions; and a pair of clamp members coupled to the elongate actuation mechanism and deployed by actuation of the elongate actuation mechanism; wherein each of the pair of clamp members comprises a retention portion configured to selectively and securely engage a threaded shaft of a pedicle screw and a portion configured to selectively and securely engage a head body of the pedicle screw, thereby holding the threaded shaft and the head body in rigid alignment; wherein each of the pair of clamp members comprises a retention portion that is configured to be selectively disposed beneath the head body of the pedicle screw and about the threaded shaft of the pedicle screw. The instrument also includes a ratcheting mechanism coupling the pair of elongate arms. The pair of clamp members are pivotably hinged to the pair of elongate arms. The pair of clamp members are pivotably hinged to one another. The pair of clamp members collectively define a void that is disposed about and substantially conforms to the head body of the pedicle screw. The elongate actuation mechanism is operable for imparting rotational motion to the pedicle screw and an individual vertebra in which the pedicle screw is implanted.

In a further exemplary embodiment, the present invention provides a pedicle screw locking and derotation method, comprising: implanting a pedicle screw in an individual vertebra of a spine; rigidly securing a head body of the pedicle screw to a threaded shaft of the pedicle screw using a pedicle screw locking and derotation instrument; and displacing the instrument laterally such that the pedicle screw is rotated about an axis of the spine, thereby rotating the individual vertebra about the axis of the spine. The instrument comprises: an elongate actuation mechanism; and a pair of clamp members coupled to the elongate actuation mechanism and deployed by actuation of the elongate actuation mechanism; wherein each of the pair of clamp members comprises a portion configured to selectively and securely engage the threaded shaft of the pedicle screw and a portion configured to selectively and securely engage the head body of the pedicle screw, thereby holding the threaded shaft and the head body in rigid alignment. The elongate actuation mechanism comprises a pair of elongate arms that are pivotably hinged to one another and comprise a pair of handle portions. The instrument also includes a ratcheting mechanism coupling the pair of elongate arms. The pair of clamp members are pivotably hinged to the pair of elongate arms. The pair of clamp members are pivotably hinged to one another. Each of the pair of clamp members comprises a retention portion that is configured to be selectively disposed beneath the head body of the pedicle screw and about the threaded shaft of the pedicle screw. The pair of clamp members collectively define a void that is disposed about and substantially conforms to the head body of the pedicle screw.

BRIEF DESCRIPTION OF THE DRAWINGS

The present invention is illustrated and described herein with reference to the various drawings, in which like reference numbers are used to refer to like instrument components, and in which.

DETAILED DESCRIPTION OF THE INVENTION

Figure 1:
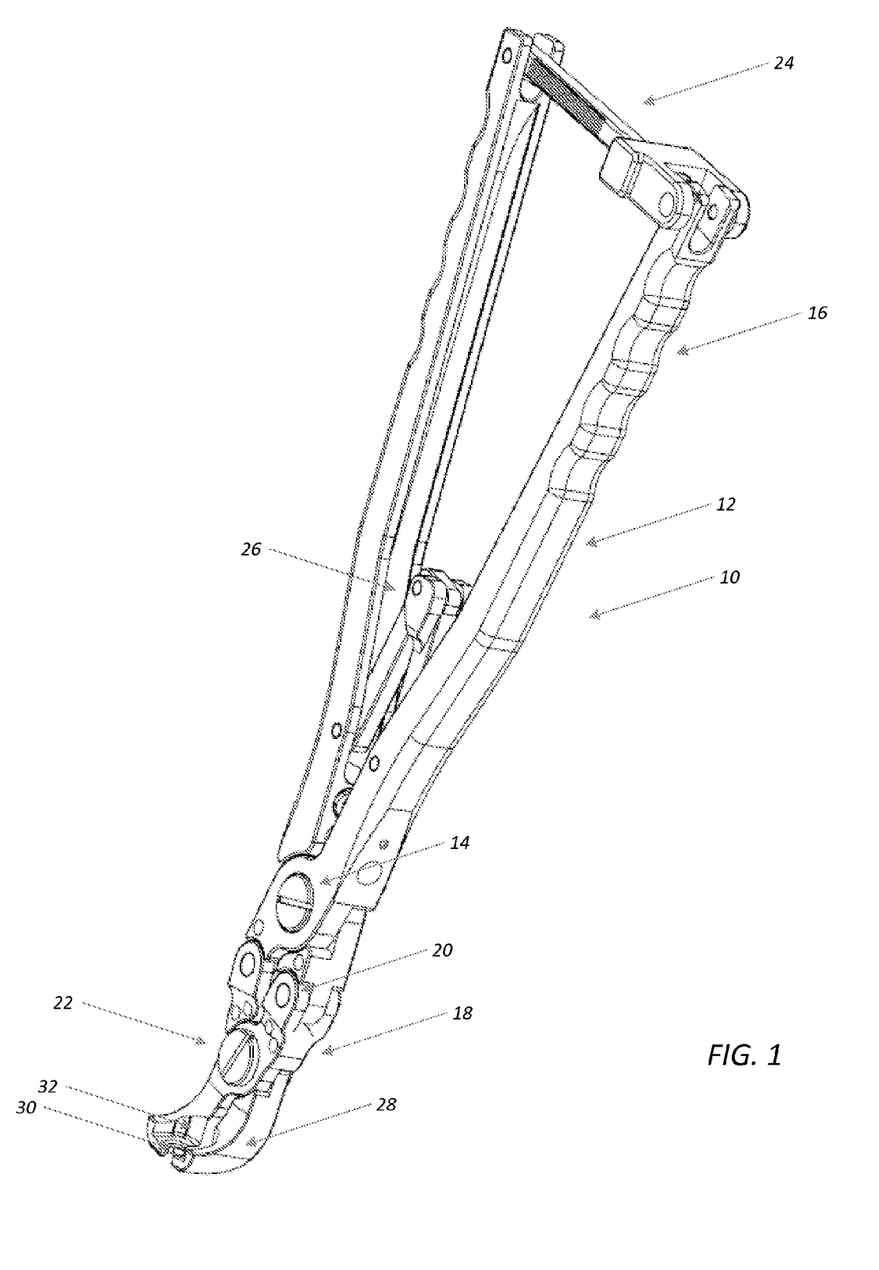
FIG. 1 is a perspective view of one exemplary embodiment of the pedicle screw locking and derotation instrument of the present invention.
Figure 2:
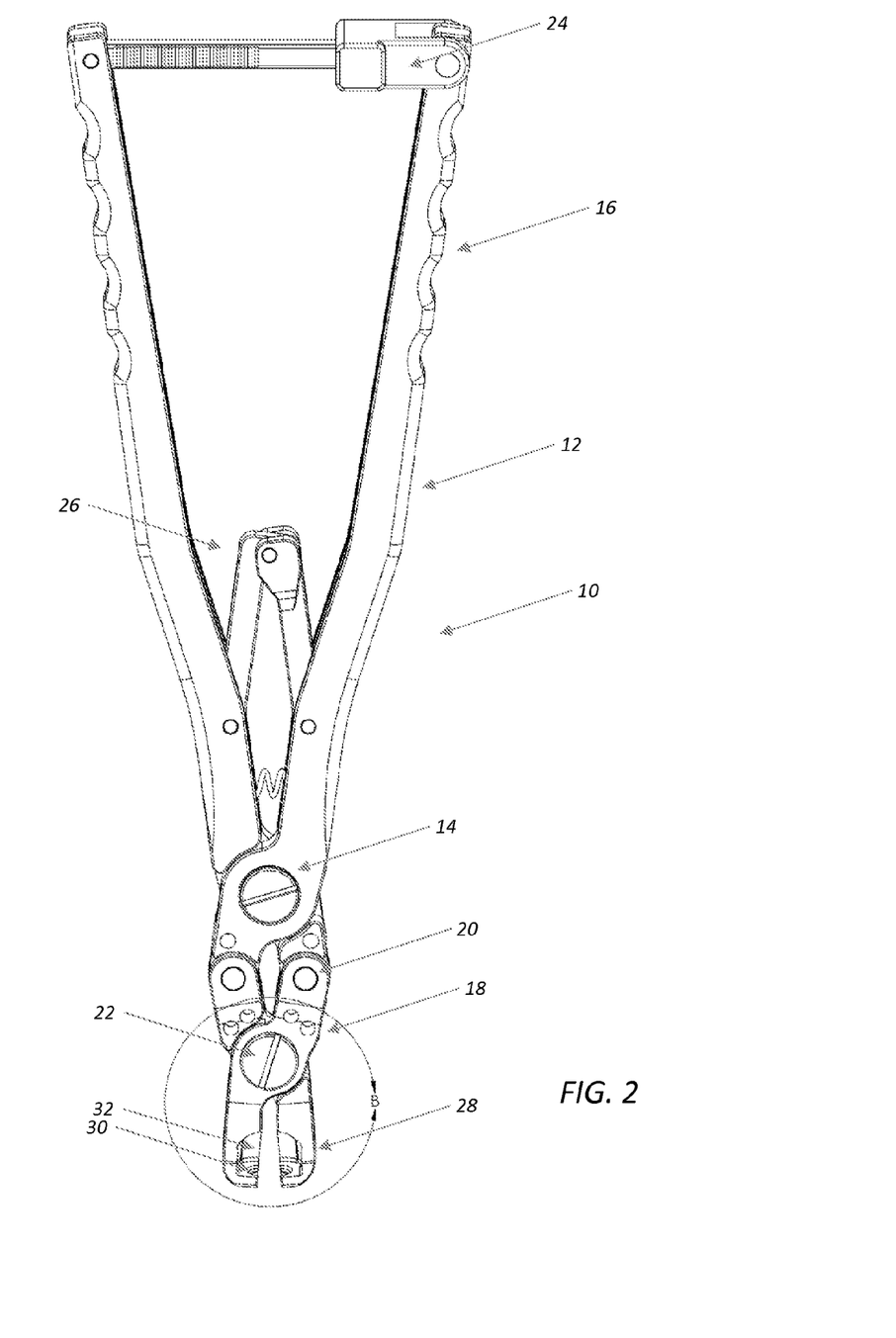
FIG. 2 is a planar view of one exemplary embodiment of the pedicle screw locking and derotation instrument of the present invention.

Referring now specifically to FIGS. 1 and 2, in one exemplary embodiment, the pedicle screw locking and derotation instrument 10 of the present invention includes a pair of elongate arms 12 that are pivotably attached to one another adjacent their proximal end. This pivotal attachment can be achieved using a screw joint 14 or any other suitable mechanism known to those of ordinary skill in the art. Each of the arms 12 includes a handle 16 at its distal end by which the arms 12 are grasped by a surgeon. Squeezing of the handles 16 together causes the arms 12 to pivot with respect to one another about the screw joint 14, thereby causing the proximal ends of the arms 12 to deflect away from one another.

Two clamp members 18 are respectively coupled to the two arms 12 via respective hinge joints 20, and to one another via a screw joint 22. The deflection of the proximal ends of the arms 12 away from one another causes the distal ends of the clamp members 18 to deflect away from one another and the clamp members to pivot about the screw joint 22. This causes the proximal ends of the clamp members 18 to deflect towards one another, such that a pedicle screw can be securely grasped by the clamp members 18 when the handles 16 of the arms 12 are squeezed together.

It will be readily apparent to those of ordinary skill in the art that any configuration that accomplishes such purpose can be used. The important aspect is that actuation of the handles 16 causes the clamp members 18 to actuate such that they securely grasp the pedicle screw. Accordingly, any configuration of ratcheting mechanisms 24 and/or stabilizing mechanisms 26 can be used to improve the function of the instrument 10, allowing it to be operated smoothly and locked into or released from a grasping configuration. This mechanism is similar to a pair of convention vise grips, well known to those of ordinary skill in the art.

The proximal end of each of the clamp members 18 includes a retention portion 28 that is disposed at an angle to the rest of the clamp member 18. Optionally, this angle is close to perpendicular. Each of the retention portions 28 includes a bottom portion 30 defining a portion of a narrowed hole that is sized and shaped to securely engage the smooth upper portion of the threaded shaft of the pedicle screw, and an interior portion 32 that is sized and shaped to securely engage the head body of the pedicle screw, such that the threaded shaft and the head body are securely held within the retention portions 28 when the clamp members 18 are engaged. Accordingly, all components of the instrument 10 are made of a metal and/or other surgically appropriate material.

Figure 3:
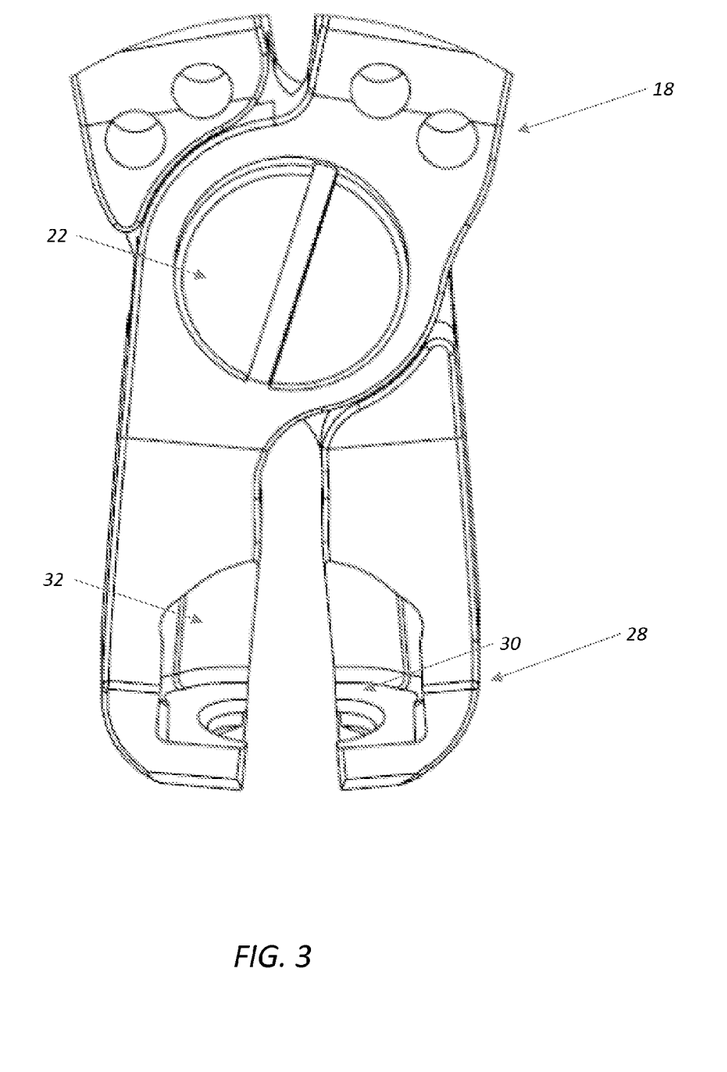
FIG. 3 is a partial planar view of one exemplary embodiment of the pedicle screw locking and derotation instrument of the present invention.

As is seen in greater detail in FIG. 3, in one exemplary embodiment, the bottom portion 30 of each of the retention members 28 defines a half-circle that, when locked together, collectively grasp and retain the smooth upper portion of the threaded shaft of the pedicle screw, which typically has a circular cross-section. In this respect, the shapes defined by the retention members substantially collectively match the cross-sectional shape of the smooth upper portion of the threaded shaft of the pedicle screw. The interior of these half-circles can include friction surfaces or an elastomeric coating that enhances this purchase. In this sense, the instrument 10 (FIGS. 1 and 2) acts like a pair of pliers for grasping the threaded shaft of the pedicles screw. The interior of each of the retention members 28 partially defines a cavity 32 that similarly securely holds the head body of the pedicle screw, the cavities 32 substantially collectively conforming to the shape of the head body. Typically, this cavity 32 defines a substantially cylindrical void that substantially matches the substantially cylindrical shape of the head body. Again, the cavities 32 can include friction surfaces or an elastomeric coating that enhances this purchase.

The key aspect is that the retention portions 28 collectively grasp and hold both the threaded shaft and the head body in rigid alignment when the retention portions 28 are deployed, preventing the head body from pivoting with respect to the threaded shaft, as would happened conventionally. Using the instrument 10, the pedicle screw can then be rigidly rotated about the axis of the spine, thereby derotating the individual vertebra in which it is implanted about the axis of the spine. This is accomplished by imparting lateral motion to the handles 16 (FIGS. 1 and 2) of the instrument 10.

Figure 4:
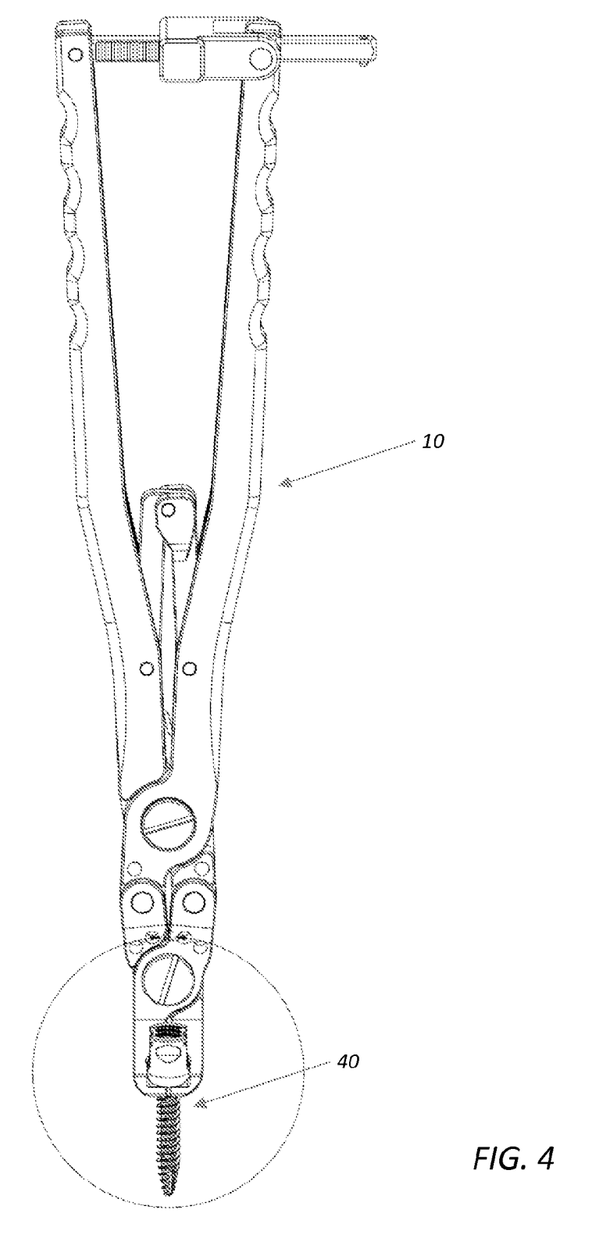
FIG. 4 is a planar view of one exemplary embodiment of the pedicle screw locking and derotation instrument of the present invention, including a manipulated polyaxial pedicle screw.
Figure 5:
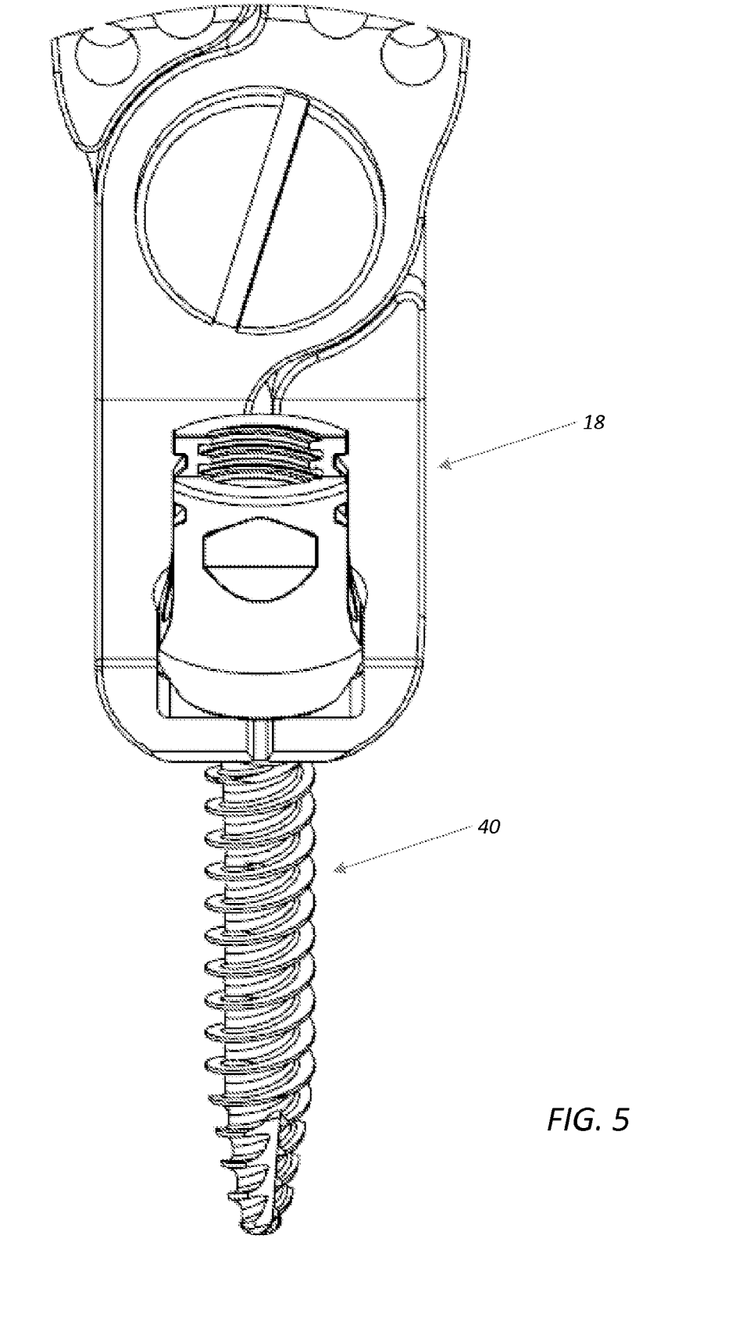
FIG. 5 is a partial planar view of one exemplary embodiment of the pedicle screw locking and derotation instrument of the present invention, including a manipulated polyaxial pedicle screw.

FIGS. 4 and 5 illustrate this exemplary embodiment of the instrument 10 (FIG. 4) and the retention members 18 with a pedicle screw 40 securely in its grasp.

Figure 6:
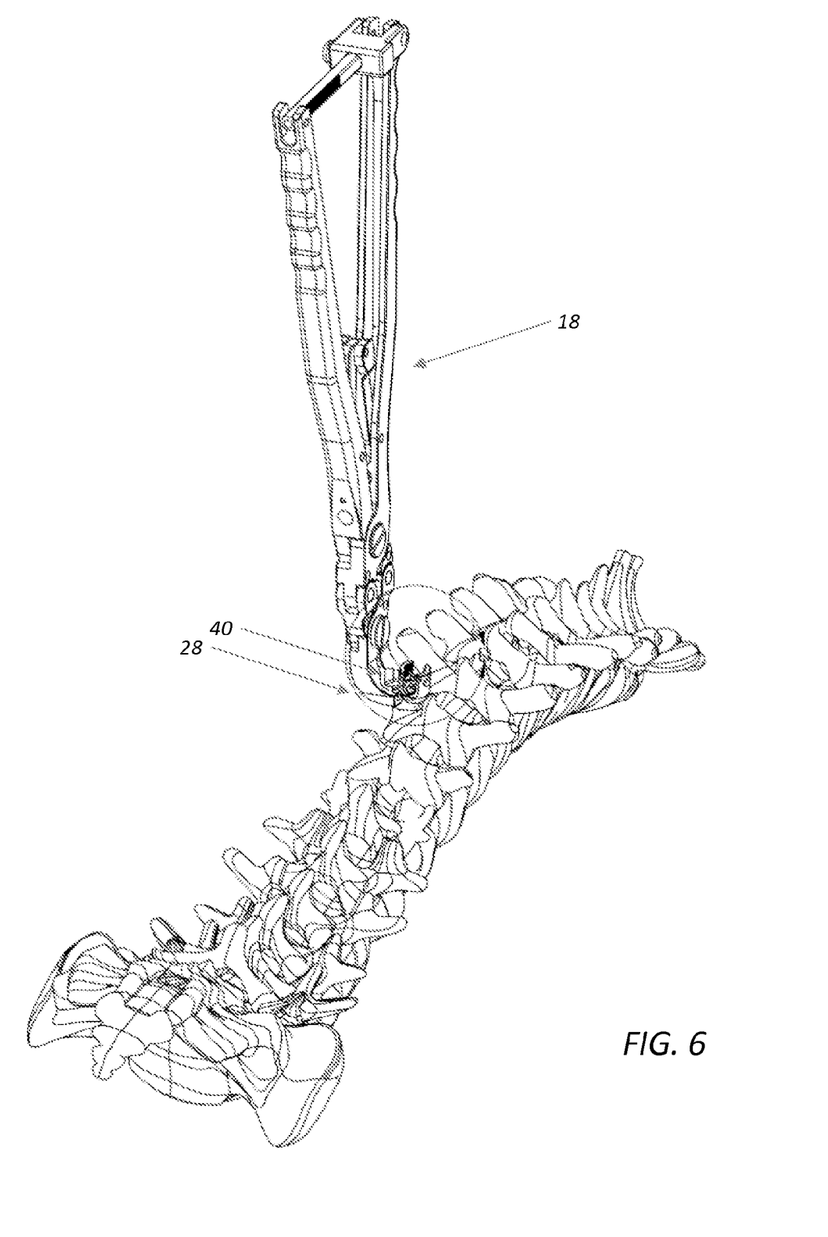
FIG. 6 is a perspective view of one exemplary embodiment of the pedicle screw locking and derotation instrument of the present invention in operation, including a manipulated polyaxial pedicle screw.
Figure 7:
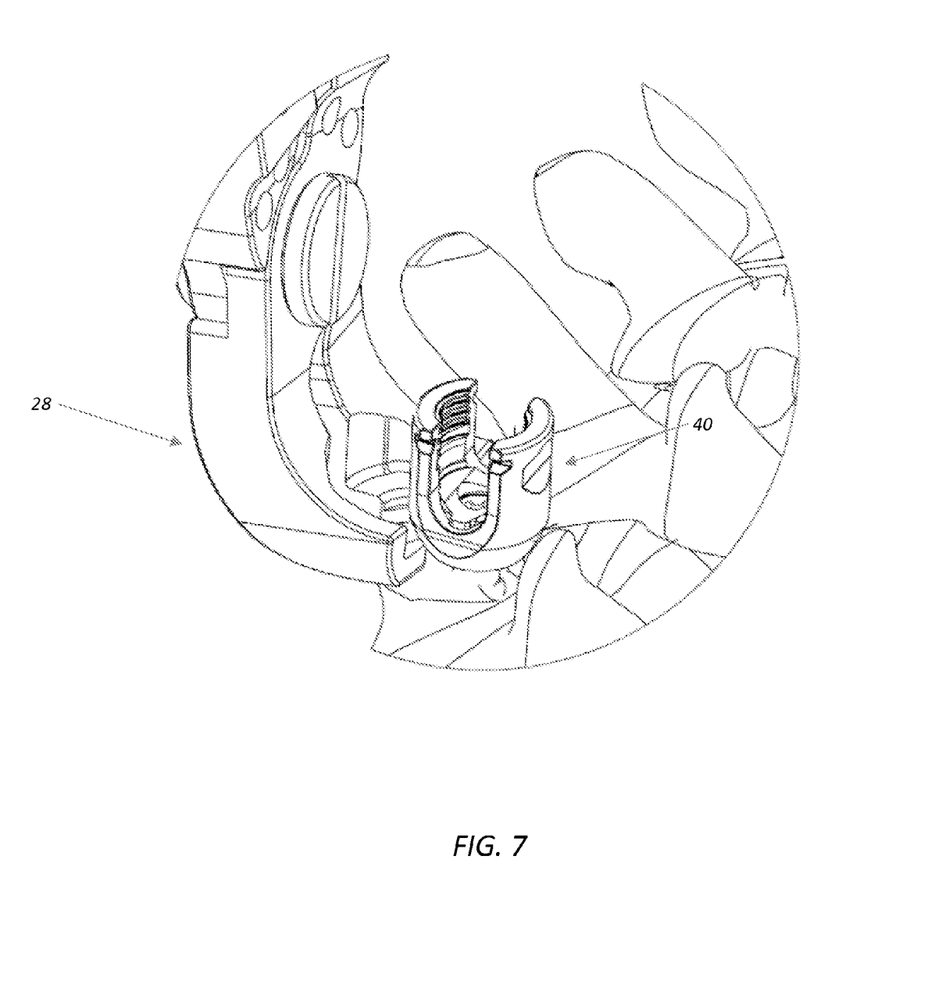
FIG. 7 is a partial perspective view of one exemplary embodiment of the pedicle screw locking and derotation instrument of the present invention in operation, including a manipulated polyaxial pedicle screw.
Figure 8:
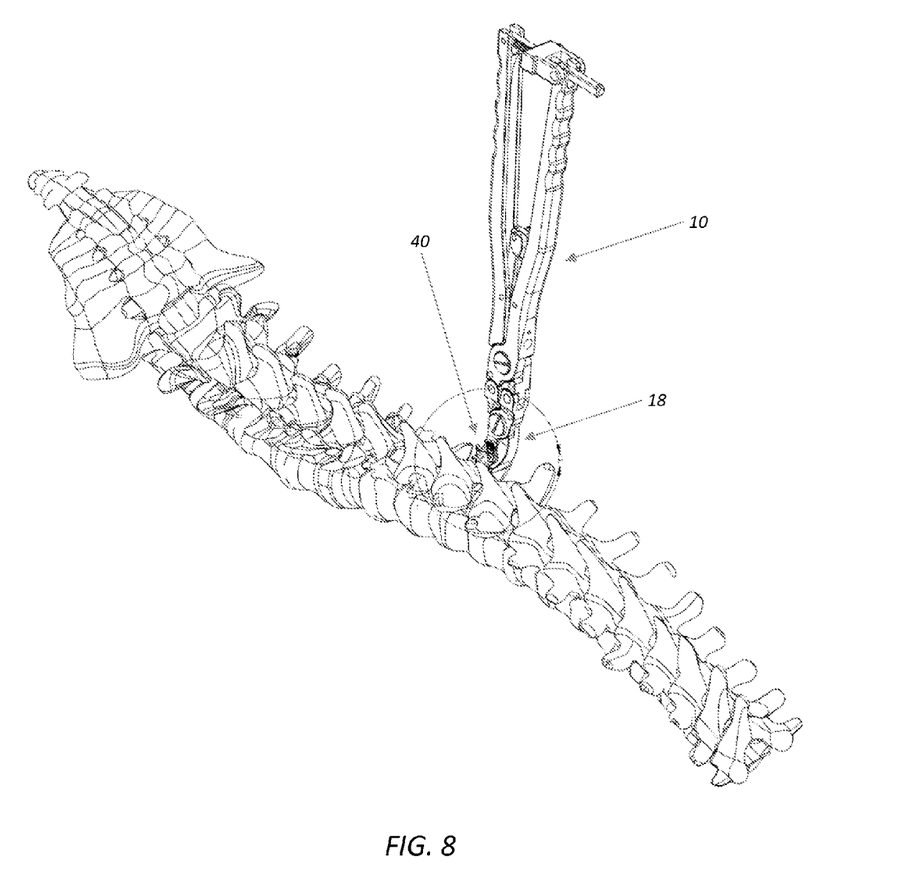
FIG. 8 is a perspective view of one exemplary embodiment of the pedicle screw locking and derotation instrument of the present invention in operation, including a manipulated polyaxial pedicle screw.
Figure 9:
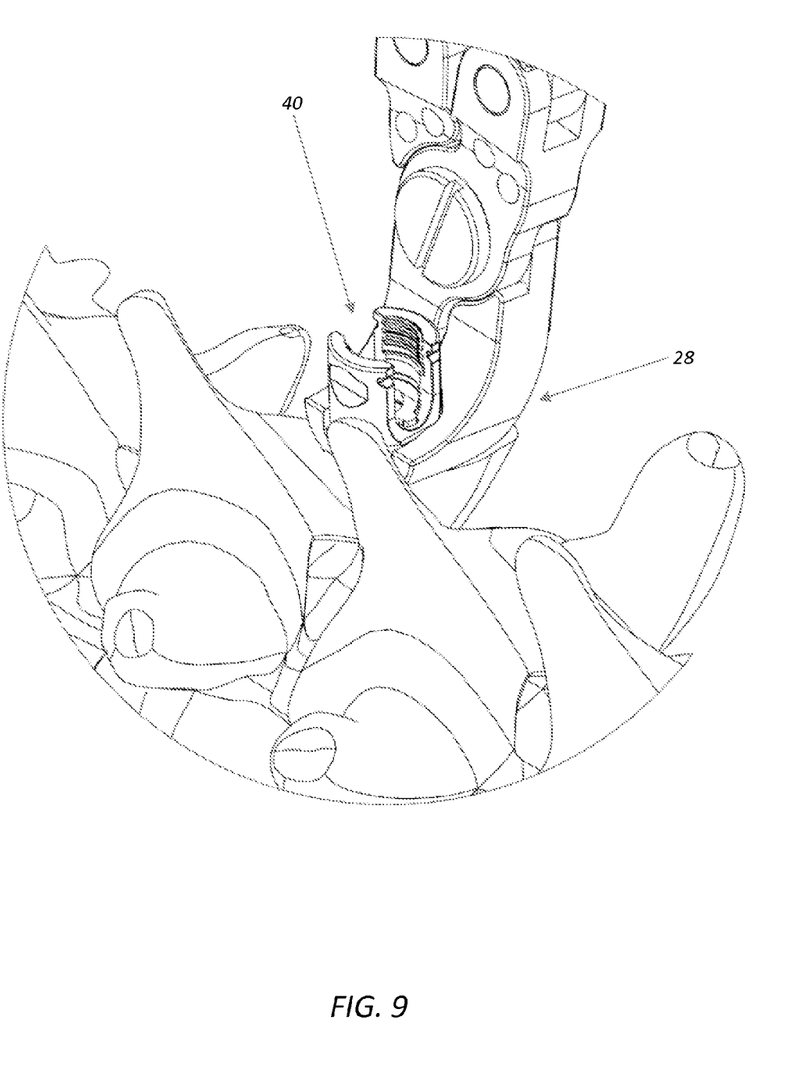
FIG. 9 is a partial perspective view of one exemplary embodiment of the pedicle screw locking and derotation instrument of the present invention in operation, including a manipulated polyaxial pedicle screw.

FIGS. 6-9 illustrate the placement and operation of the instrument 10. Specifically, FIGS. 6 and 7 illustrate the instrument 10 in an open configuration, with the clamp members 18 and the retention members 28 being deployed away from one another as the retention members 28 are slid about the threaded shaft of the pedicle screw 40 beneath the head body. Referring to FIGS. 8 and 9, the clamp members 18 and the retention members 28 are then closed around the threaded shaft and head body of the pedicle screw 40, securely grasping the pedicle screw 40 and holding it in a fixed configuration, with no relative pivotal movement between the head body and the threaded shaft.

Figure 10:
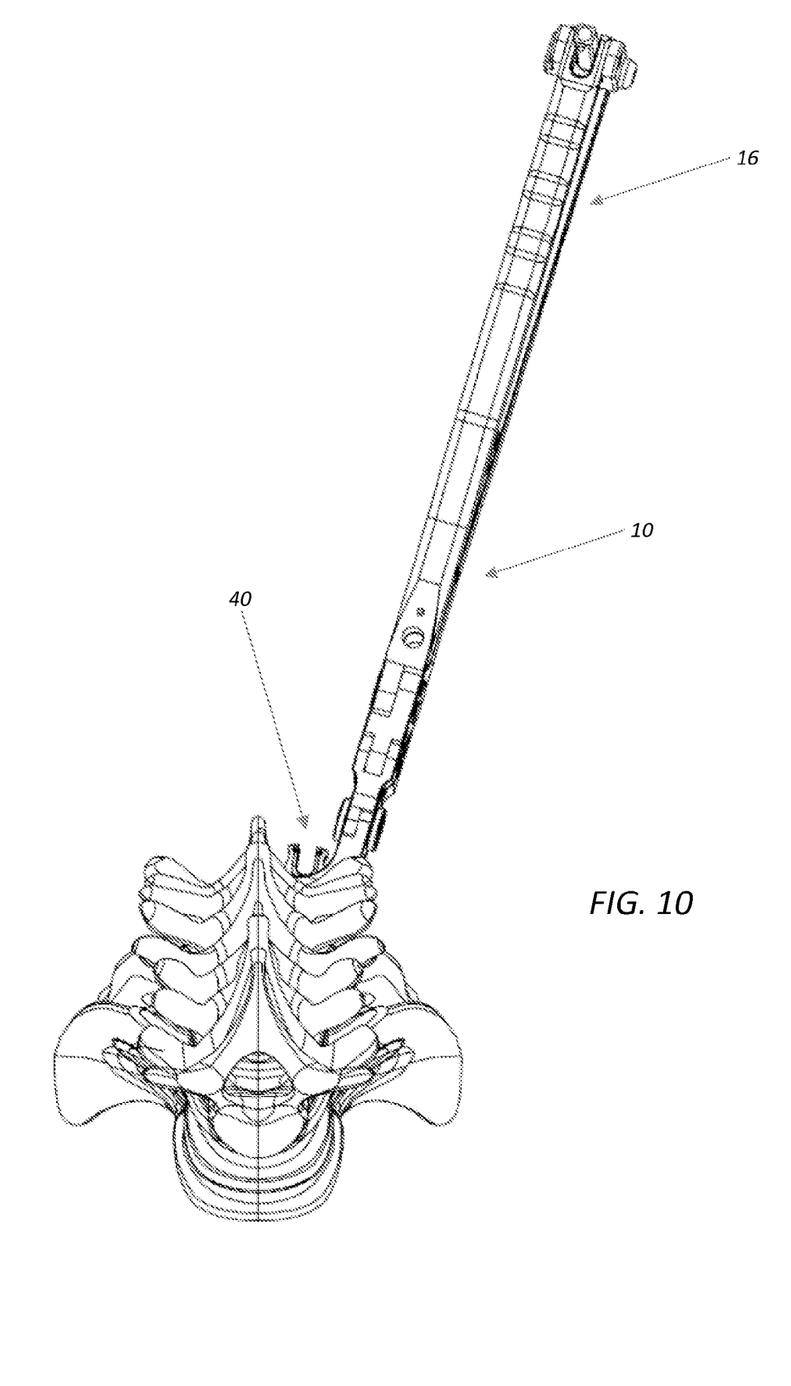
FIG. 10 is a perspective view of one exemplary embodiment of the pedicle screw locking and derotation instrument of the present invention in operation, including a manipulated polyaxial pedicle screw.
Figure 11:
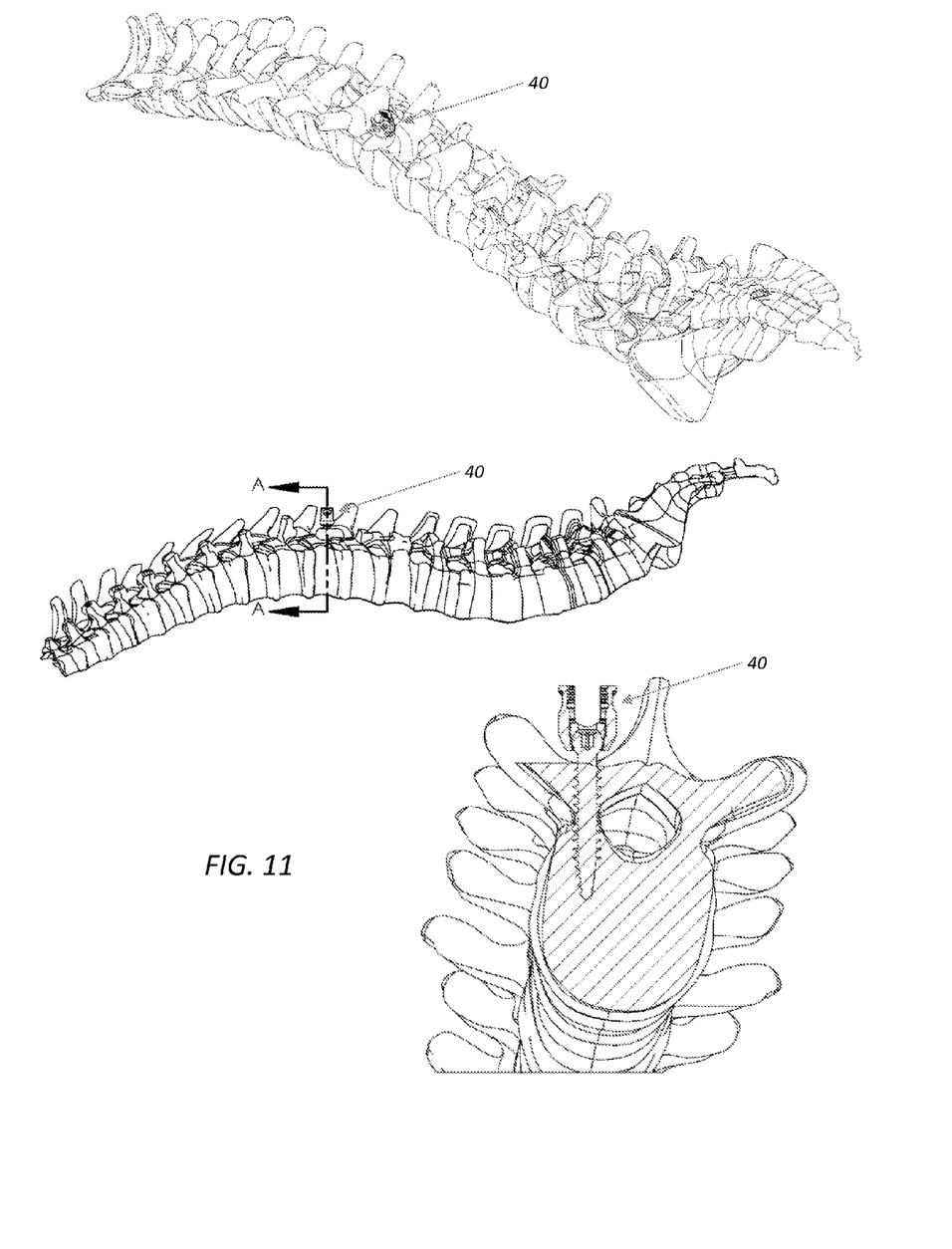
FIG. 11 is a series of perspective, planar, and axial views of a polyaxial pedicle screw placed using the pedicle screw locking and derotation instrument of the present invention.

FIGS. 10 and 11 illustrate the derotation of the individual vertebra accomplished using the instrument 10. Essentially, once the pedicle screw 40 is grasped and the instrument is locked, the pedicle screw 40 implanted in the individual vertebra acts as a rigid lever arm by which the individual vertebra is derotated. This is accomplished by pushing the handles 16 (FIG. 10) of the instrument 10 (FIG. 10) laterally about the axis of the spinal column.

It should be noted that the exterior surfaces of the clamp members 18 can have substantially smooth and curved shapes such that the do not interfere with or snag on any anatomical structures. This is especially true where the clamp members 18 merge into the retention members 28.

Although the present invention is illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the present invention, are contemplated thereby, and are intended to be covered by the following non-limiting claims.

What is claimed is:

1. A pedicle screw locking and derotation instrument, comprising:
    an elongate actuation mechanism; and
    a pair of clamp members coupled to the elongate actuation mechanism and deployed by actuation of the elongate actuation mechanism;
    wherein each of the pair of clamp members comprises a portion configured to selectively and securely engage a threaded shaft of a pedicle screw and a portion configured to selectively and securely engage a head body of the pedicle screw, thereby holding the threaded shaft and the head body in rigid alignment;
    wherein each of the pair of clamp members comprises a retention portion that is configured to be selectively disposed beneath the head body of the pedicle screw and about the threaded shaft of the pedicle screw; and
    wherein the retention portion is disposed at an angle to the remainder of each of the pair of clamp members and defines a half-circle interior portion that is configured to engage the threaded shaft of the pedicle screw.

2. The instrument of claim 1, wherein the elongate actuation mechanism comprises a pair of elongate arms that are pivotably hinged to one another and comprise a pair of handle portions.

3. The instrument of claim 2, further comprising a ratcheting mechanism coupling the pair of elongate arms.

4. The instrument of claim 2, wherein the pair of clamp members are pivotably hinged to the pair of elongate arms.

5. The instrument of claim 1, wherein the pair of clamp members are pivotably hinged to one another.

6. The instrument of claim 1, wherein the pair of clamp members collectively define a void that is disposed about and substantially conforms to the head body of the pedicle screw.

7. The instrument of claim 1, wherein the elongate actuation mechanism is operable for imparting rotational motion to the pedicle screw and an individual vertebra in which the pedicle screw is implanted.

8. A pedicle screw locking and derotation instrument, comprising:
    an elongate actuation mechanism, wherein the elongate actuation mechanism comprises a pair of elongate arms that are pivotably hinged to one another and comprise a pair of handle portions; and a pair of clamp members coupled to the elongate actuation mechanism and deployed by actuation of the elongate actuation mechanism;

wherein each of the pair of clamp members comprises a retention portion configured to selectively and securely engage a threaded shaft of a pedicle screw and a portion configured to selectively and securely engage a head body of the pedicle screw, thereby holding the threaded shaft and the head body in rigid alignment;

wherein each of the pair of clamp members comprises a retention portion that is configured to be selectively disposed beneath the head body of the pedicle screw and about the threaded shaft of the pedicle screw; and wherein the retention portion is disposed at an angle to the remainder of each of the pair of clamp members and defines a half-circle interior portion that is configured to engage the threaded shaft of the pedicle screw.

9. The instrument of claim 8, further comprising a ratcheting mechanism coupling the pair of elongate arms.

10. The instrument of claim 8, wherein the pair of clamp members are pivotably hinged to the pair of elongate arms.

11. The instrument of claim 8, wherein the pair of clamp members are pivotably hinged to one another.

12. The instrument of claim 8, wherein the pair of clamp members collectively define a void that is disposed about and substantially conforms to the head body of the pedicle screw.

13. The instrument of claim 8, wherein the elongate actuation mechanism is operable for imparting rotational motion to the pedicle screw and an individual vertebra in which the pedicle screw is implanted.

14. A pedicle screw locking and derotation method, comprising:
  implanting a pedicle screw in an individual vertebra of a spine;
  rigidly securing a head body of the pedicle screw to a threaded shaft of the pedicle screw using a pedicle screw locking and derotation instrument; and
  displacing the instrument laterally such that the pedicle screw is rotated about an axis of the spine, thereby rotating the individual vertebra about the axis of the spine;

wherein the instrument comprises:

an elongate actuation mechanism; and a pair of clamp members coupled to the elongate actuation mechanism and deployed by actuation of the elongate actuation mechanism;

wherein each of the pair of clamp members comprises a portion configured to selectively and securely engage the threaded shaft of the pedicle screw and a portion configured to selectively and securely engage the head body of the pedicle screw, thereby holding the threaded shaft and the head body in rigid alignment;

wherein each of the pair of clamp members comprises a retention portion that is configured to be selectively disposed beneath the head body of the pedicle screw and about the threaded shaft of the pedicle screw; and wherein the retention portion is disposed at an angle to the remainder of each of the pair of clamp members and defines a half-circle interior portion that is configured to engage the threaded shaft of the pedicle screw.

15. The method of claim 14, wherein the elongate actuation mechanism comprises a pair of elongate arms that are pivotably hinged to one another and comprise a pair of handle portions.

16. The method of claim 15, further comprising a ratcheting mechanism coupling the pair of elongate arms.

17. The method of claim 15, wherein the pair of clamp members are pivotably hinged to the pair of elongate arms.

18. The method of claim 14, wherein the pair of clamp members are pivotably hinged to one another.

19. The method of claim 14, wherein the pair of clamp members collectively define a void that is disposed about and substantially conforms to the head body of the pedicle screw.

* * * * *